(12) United States Patent
Conoci et al.

(10) Patent No.: US 7,799,912 B2
(45) Date of Patent: Sep. 21, 2010

(54) BIFUNCTIONAL CHEMICAL, PREPARATION AND USE FOR DETECTING NUCLEIC ACID

(75) Inventors: Sabrina Conoci, Tremiestieri Etneo (IT); Salvatore Sortino, Tremiestieri Etneo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 357 days.

(21) Appl. No.: 11/875,755

(22) Filed: Oct. 19, 2007

(65) Prior Publication Data

US 2008/0118405 A1    May 22, 2008

(30) Foreign Application Priority Data

Oct. 19, 2006    (IT)    ................ TO2006A000754

(51) Int. Cl.
*C07D 279/00*    (2006.01)
*C12Q 1/68*    (2006.01)
*G01N 15/06*    (2006.01)
*C07H 21/04*    (2006.01)

(52) U.S. Cl. ................ 544/14; 435/6; 536/24.3; 536/26.6; 422/681

(58) Field of Classification Search ........ 435/6; 536/24.3, 26.6; 422/68.1; 544/14
See application file for complete search history.

(56) References Cited

U.S. PATENT DOCUMENTS

| | | |
|---|---|---|
| 2001/0014452 A1 | 8/2001 | Makino et al. |
| 2001/0053522 A1 * | 12/2001 | Makino et al. ........ 435/6 |
| 2002/0117396 A1 | 8/2002 | Pak et al. |

FOREIGN PATENT DOCUMENTS

| | | |
|---|---|---|
| EP | 07118929 | 3/2008 |
| JP | 2000-125865 | 5/2000 |
| JP | 2000-146894 | 5/2000 |
| WO | WO02/063041 | 8/2002 |
| WO | WO2006030788 | 3/2006 |

OTHER PUBLICATIONS

J. Joseph, et al., Control of electron-transfer and DNA Binding Properties by the tolyl spacer group in viologen linked acridines. J. Phys. Chem. 107: 4444-4450 (2003).

(Continued)

*Primary Examiner*—Jezia Riley
(74) *Attorney, Agent, or Firm*—Baker & McKenzie LLP (57) ABSTRACT

A bifunctional compound comprising a molecular unit (I) intercalating between nucleobases (B) of nucleic acids, an active molecular unit (AD) capable of emitting a detectable signal, and optionally a spacer unit, in which the active molecular unit (AD) is selected from amongst chemical entities having a structure such as to interact electronically with the intercalating molecular unit (I) in such a way that, during the reaction of oxidation, the reduction-oxidation potential (EI+/I) of the semicouple I+/I defined by the intercalating molecular unit (I) is lower than the reduction-oxidation potential (EB+/B) of the semicouple B+/B defined by the nucleobases (B), and in such a way that, during the reaction of reduction, the reduction-oxidation potential (EI/I−) of the semicouple I/I− defined by the intercalating molecular unit (I) is higher than the reduction-oxidation potential (EB/B−) of the semicouple B/B− defined by the nucleobases (B). Moreover the use of the compound for detecting nucleic acids, a process for its synthesis, and a system comprising the same are described.

16 Claims, 11 Drawing Sheets

(1)

OTHER PUBLICATIONS

Kumar, C.V., et al., Sequence dependent energy transfer from DNA to a simple aromatic chromophore. J. Chem. Soc., Chem. Commun. p. 470-472 (1992).

McGhee, J.D., et al., Theoretical aspects of DNA-protein interactions: co-operative and non-co-operative binding of large ligands to a one-dimensional homogenous lattice. J. Mol. Biol. 86:469-489 (1974).

Pang, D., et al., Interactions of benzyl viologen with surface-bound single- and double-stranded DNA. Anal. Chem. 72:4700-4706 (2000).

Takagi, M., Threading intercalation to double-stranded DNA and the application to DNA sensing. Electrochemical array technique. Pure Appl. Chem. 73:1573-1577 (2001).

Akira, T., et al., Thermodynamic parameters for formation of through-ring alpha-cyclodextrin complexes of donor-acceptor linked compounds: comparison between deuterium oxide and water solutions of anthrcene-viologen systems with intramolecular charge-transfer absorption spectra. Bulletin of the Chemical Society of Japan 66:3382-3386 (1993), CAPLUS accession No. 1994:164699.

Substance identification, Beilstein Institute for Organic Chemistry, accession No. Beilstein Registry No. (BRN) 7405708, 2007.

Ashton, P.R., et al., Acid-base controllable molecular shuttles. J. Am. Chem. Soc. 120: 11932-11942 (1998).

Deng, N., et al., A new chiral cyclophane derived from 1,1'-binaphthol and benzylviolgen. Tetrahedron letters 36:7599-7602 (1995).

Effenberger, F., et al., Synthesis and Properties of alpha-bridged anthracene viologens. Chemische Berichte 125:941-952, (1992).

Park, J.W., et al., Linkage length dependence of intramolecular photoinduced electron transfer reactions in aromatic donor-viologen acceptor molecules linked by polymethylene bridges. J. Phys. Chem. Part B. 102:8209-8215 (1998).

Armitage, B., Photocleavage of nucleic acids. Chem. Rev. 98: 1171-1200 (1998).

Dunn, D.A., et al., Base-selective oxidation and cleavage of DNA by photochemical cosensitized electron transfer. Biochemistry 31:11620-11625 (1992).

Le, T.P., et al., Photoinduced electron transfer in covalently linked 1,8-naphthalimide/viologen systems. J. Phys. Chem. A. 104:6778-6785 (2000).

* cited by examiner

BIFUNCTIONAL CHEMICAL, PREPARATION AND USE FOR DETECTING NUCLEIC ACID

PRIOR RELATED APPLICATIONS

This application claims priority to Italian Patent Application No. TO2006A000754, filed on Oct. 19, 2006 in the name of STMicroelectronics S.r.l., and is incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to a bifunctional chemical compound, its preparation and use for the detection of nucleic acids, and to a system comprising the same.

BACKGROUND OF THE INVENTION

Detection of nucleic acid is commonly carried out employing so-called "DNA chips," which are amenable to high throughput and are more reliable than conventional Southern or Northern blot techniques. Generally, such chips have numerous oligonucleotide fragments ("probes") of known sequence, and for improved stability it is usually preferred that the probes be either DNA or modified oligonucleotides that are resistant to chemical and enzymatic degradation. During analysis, samples to be investigated are placed in contact with the chip so as to enable hybridization of the probes with the sample DNA or RNA to be analyzed. Next, the hybridized nucleic acid is detected and quantified by some method, usually an optical method using intercalating dyes or other fluorescent labels.

However, such techniques require the use of optical devices and/or fluorescent markers that are very costly. In addition, a quantitative determination of the target DNA present in the sample is difficult. Consequently alternative methods have been studied for detecting chains of DNA on DNA chips, for example of electrochemical type, which make use of the bifunctional compounds.

Figure 1:
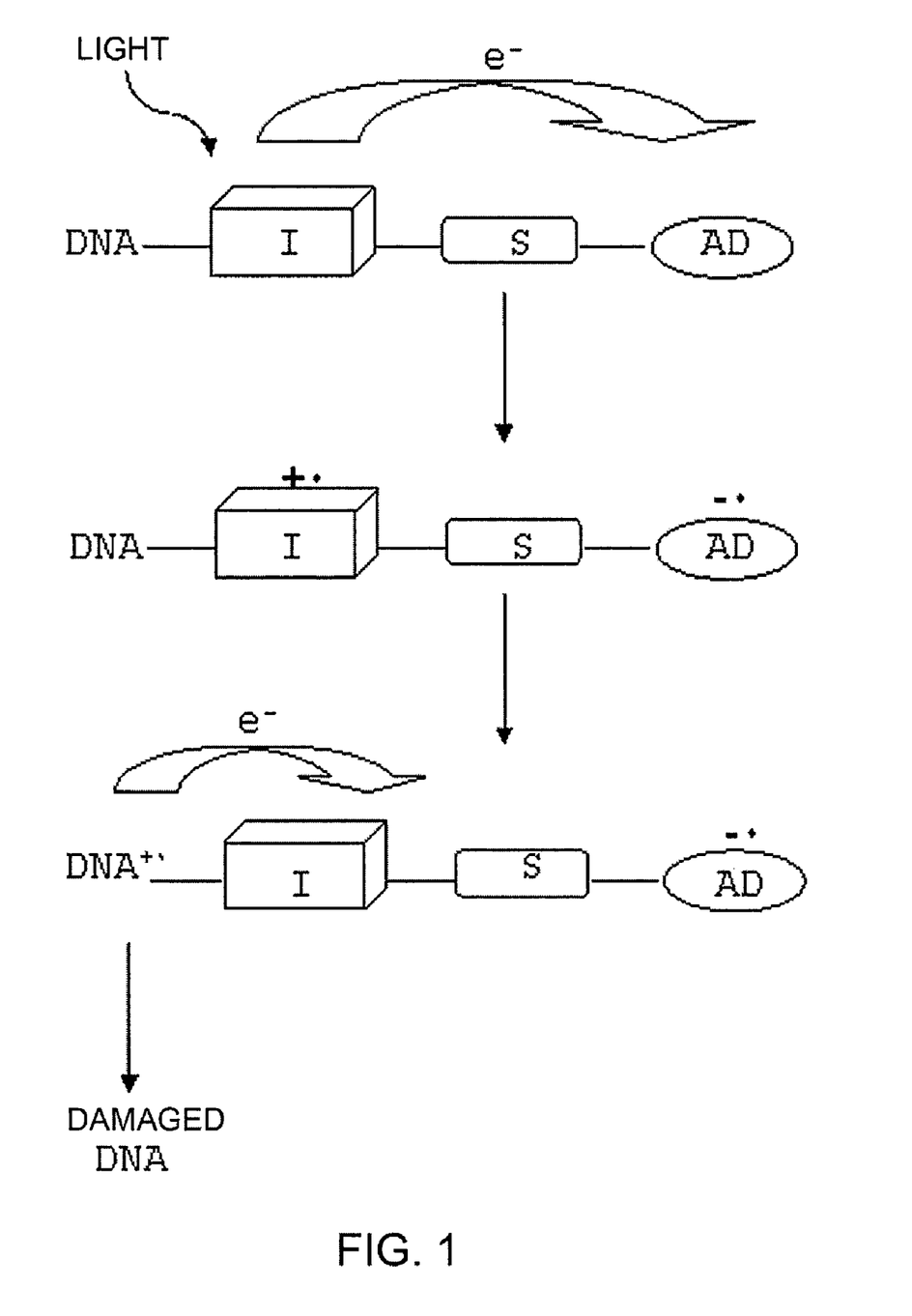
FIG. 1 illustrates the mechanism of activation of a bifunctional compound according to the state of the art.

Bifunctional compounds are currently used for photocleavage of DNA and have two molecular units—one referred to as "intercalating" unit (I) and the other as "active unit" (AD). Generally, the unit I is oxidized by light irradiation so that it transfers one electron to the unit AD. Next, the oxidized unit I is reduced by the DNA before the electron donated to the unit AD returns to the unit I. This mechanism leads to oxidation of the DNA and hence to cleavage thereof as illustrated in FIG. 1 (J. Joseph, et al., J. Phys. Chem. B (2003), volume 107, pages 4444-4450 and references given therein).

It has been found, however, that some bifunctional compounds can also be used for detection of nucleic acids.

Japanese patent No. JP2000-125865 describes a method for detecting a gene by hybridizing it with a DNA probe immobilized on an electrode in presence of an intercalating compound with electrochemical properties, namely, N—N-bis[[4-(3-ferrocenecarboxaminopropyl)piperazinyl]propyl] naphthalen-1,4,5,8-tetracarboxylic acid.

Other examples of intercalating bifunctional compounds for electrochemical detection of chains of double-strand DNA are described in Makoto Takagi, Pure Appl. Chemistry, 2001, vol. 10, pages 1573-1577, where the intercalating unit I is naphthalendiimide and the active unit AD is ferrocene, or in US2002117396, where the compound is N-[3-[4-(3-ferrocenecarboxamidopropyl)piperazinyl]propyl]-1,8-naphthalenimide.

In the bifunctional compounds referred to above, the intercalating unit I can absorb environmental light. Consequently, in appropriate thermodynamic conditions, these compounds can undergo photoinduced processes of electron transfer, which can lead to damage of the DNA as described for the methods of DNA cleavage (J. Joseph, N. V. Eldho, D. Ramaiah, J. Phys. Chem. B (2003), vol. 107, pages 4444-4450 and references contained therein), rendering the DNA unusable for further subsequent analyses or even yielding unreliable analytical results.

Consequently, the known bifunctional compounds must be used in detection applications where appropriate conditions of light are guaranteed and are therefore not suitable for extensive use in industry.

The aim of the present invention is hence to provide light stable bifunctional compounds suitable for use in the analysis of nucleic acids.

SUMMARY OF THE INVENTION

According to the present invention, a bifunctional compound is provided, comprising a intercalating unit (I) that can intercalate between the nucleobases (B) of nucleic acids, an active detection unit (AD), capable of emitting a detectable signal, and optionally a spacer unit, in which the active detection unit (AD) is selected from amongst chemical entities having a structure such as to interact electronically with the intercalating unit (I) in such a way that, during the reaction of oxidation, the reduction-oxidation potential (EI+/I) of the semicouple I+/I defined by the intercalating unit I is lower than the reduction-oxidation potential (EB+/B) of the semicouple B+/B defined by the nucleobases B, while, during the reaction of reduction, the reduction-oxidation potential (EI/I) of the semicouple I/I− defined by the intercalating I is higher than the reduction-oxidation potential (EB/B−) of the semicouple B/B− defined by the nucleobases B.

This particular arrangement of bifunctional components having an intercalating portion (I) and an active detection portion (AD) allows the bifunctional molecule to bind to nucleic acid bases (B), absorb energy and transfer that energy to the active detection portion, which then produces a detectable signal. However, redox potential of the various portions or components is arranged so that energy is not transferred to the bases, but instead to the active detection portion, thus avoiding the changes to DNA structure that normally result in strand cleavage. Therefore, the bifunctional compound allows detection of nucleic acid without compromising the structure of the nucleic acid.

Detectors may contain a plurality of electrodes coated with or nearby one or more probes. When the probes hybridize with the target and bind the bifunctional compound, the current will increase at that site. The current density depends on the concentration of the target nucleic acid in the sample, thus it is possible to quantify the amount thereof. The current density may be measured by any method, e.g., cyclic voltametry, differential pulse voltametry and potentiostat.

Hereinafter, the term "chemical entities" means portions of molecules comprising functional groups or else entire molecules comprising functional groups.

The intercalating unit I of the bifunctional compounds has a structure such as to bind the nucleic acids by overlapping the π orbitals with the nucleobases B, and is preferably selected in the group consisting of a naphthalene group, an anthracene group, a pyrene group, a phenanthrene group, and functionally equivalent compounds.

The active detection unit AD is chosen from among the chemical entities capable of emitting a detectable signal chosen from amongst a luminescent signal, a magnetic signal, an electrical signal, a thermal signal, an optical signal, an electronic signal, and an electrochemical signal, and has, for example, the chemical structure of viologen. The viologens are diquaternary derivatives of 4,4'-bipyridyl. The name comes from the fact that this class of compounds is easily reduced to the radical mono cation, which is intensely blue colored. The general formula of a viologen is 1,1'-di-r-4,4'-bipyridinium chloride, where r=methyl, ethyl, benzyl or, betaine. Ruthenium II complex with bipyridile and general electrochromic metallic complexes or bipolar complexes may be also used.

In the present context, it is important for the signal emitted by the active detection unit AD to be detectable using techniques that do not alter the DNA structure.

The spacer unit S, when present, prevents the direct electron interaction between the intercalating unit I and the active detection unit AD in the ground state and is a non-conjugated system, for example, an optionally substituted aliphatic chain, in particular, an aliphatic chain substituted with derivatives of para-xylene. The spacer can be also an aliphatic alkyl chain.

In particular, the present bifunctional compound is provided with an active detection unit AD with a structure such as to de-activate the excited state of the intercalating unit I by transfer of electrons, thus preventing any further interaction between the excited state of the intercalating unit I and the nucleobases B of the DNA chain.

Consequently, the intercalating unit I, stabilized by the appropriate active detection unit AD, has a reduction-oxidation potential lower than that of the nucleobases, so as to not favor processes of electron exchange and thus prevent cleavage of the nucleic acid.

The claimed bifunctional molecule structure is advantageous because the appropriate choice of the intercalating unit I and of the active detection unit AD allow optimization of the sensitivity and specificity of detection of the nucleic acids, but still prevent degradation thereof.

Figure 11:
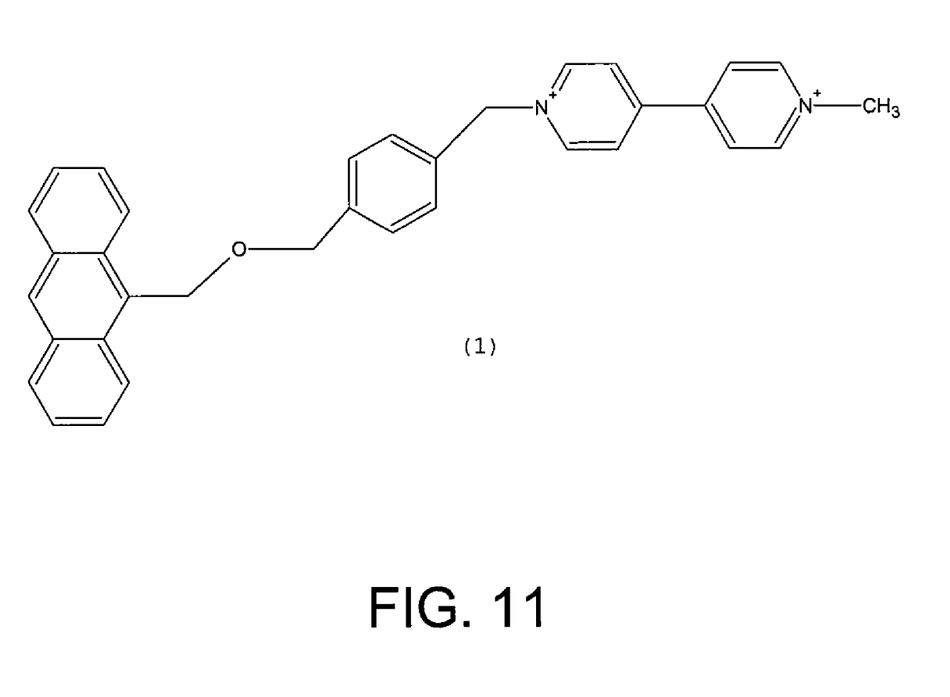
FIG. 11 is the compound of Formula 1.

In particular, a bifunctional chemical compound, namely, 1-{4-[2-(9-anthrylmethoxy)ethyl]benzyl}-1'-methyl-4,4'-bipiridinium is provided having Formula 1 as shown in FIG. 11:

(1)

The compound of Formula 1 is made up of an intercalating unit I containing anthracene, known for its dsDNA intercalating activity and by an active unit AD containing a viologen, known for its capability of undergoing reversible reduction.

The anthracene function, in the excited state following upon a light stimulus, can be deactivated using a process of electron transfer by photoreduction by the viologen, which, by undergoing reduction, prevents any further electron transfer towards the nucleic acids in which the anthracene is intercalated.

The compound of Formula 1 is synthesized using a process that comprises the steps of reacting a compound of Formula 2:

(2)

where n is 0-10, with a para-xylene substituted in the positions α,α' with a halogen in the presence of sodium hydride to obtain a compound of Formula 3;

(3)

where X is a halogen; reacting the compound of Formula 3 with a 4,4'-bipyridyl to obtain a compound of Formula 5;

(5)

and finally, reacting the compound of Formula 5 with a halogenated derivative of methane to obtain the compound of Formula 1.

The present bifunctional compounds are particularly suitable for use in detection of nucleic acids, for example for an electrochemical detection. In addition, it is possible to analyze nucleic acids of different nature such as RNA and single-strand or double-strand DNA either in solution or immobilized on a solid surface following upon hybridization with nucleic acid probes.

The present bifunctional compounds can be used for distinguishing between single-strand or double-strand DNA chains.

Finally, according to the present invention, a system is provided for detecting nucleic acids, comprising a bifunctional compound as defined above, means for detecting the signal emitted by the active detection unit AD of the bifunctional compound and nucleic acid probes. In addition, the system can comprise supporting means for the nucleic acid probes.

BRIEF DESCRIPTION OF THE DRAWINGS

Further characteristics and advantages of the present invention will emerge from the following description of some embodiments thereof, which are provided merely by way of non-limiting illustration, with reference, wherever necessary, to the annexed drawings, wherein.

DESCRIPTION OF EMBODIMENTS OF THE INVENTION

In particular, with reference to FIGS. 9 and 10, a system or device for detecting nucleic acids, designated as a whole by the reference number 11, comprises a bifunctional compound 12 according to the present invention (see examples below); detection means 13, for example a system of electrodes; and nucleic acid probes 14, for example immobilized on a support 15. At the moment of the analysis, a sample nucleic acid 16 that is to be analyzed is added to the detection device 11 and allowed to contact the probes 14. During or after hybridization, the bifunctional compound 12 intercalates between the double strands of nucleic acid and emits a signal that can be detected by the detection means 13. The signal emitted by the viologen can have two components: 1) and electrical signal connected to its reduction potential; and 2) an optical signal (easy to be detected in case of transparent electrodes) due to the coloring of the viologen; the color remains until a potential to stabilize the reduced form is applied.

Any detector means suitable known in the art can be employed with the invention. One example is the electrochemical detector, another is the optical detector, and combinations are also possible. The electrochemical detector responds to substances that are either oxidizable or reducible and the electrical output is an electron flow generated by a reaction that takes place at the surface of the electrodes. Generally speaking, the electrochemical detector requires three electrodes, the working electrode (where the oxidation or reduction takes place), the auxiliary electrode and the reference electrode (which compensates for any changes in the background conductivity of the mobile phase). If the reaction proceeds to completion (exhausting all the reactant) the current becomes zero and the total charge generated will be proportional to the total mass of material that has been reacted. This process is called coulometric detection. If, however, the mobile phase is flowing past the electrodes, the reacting solute will be continuously replaced as the peak passes through the detector. All the time there is solute present between the electrodes, a current will be maintained, albeit varying in magnitude. Until relatively recently, this procedure was that most common employed in electrochemical detection and is called amperometric detection. Other methods measure direct oxidation of nucleic acid, and yet another uses redox enzymes as the labels.

Other electrochemical detectors include those that measure capacitance. Capacitance at a surface is determined by the existence of charge and the ability of the region near the surface to charge or discharge. Capacitance at the surface with single-stranded DNA will be different from hybridized double-stranded DNA. By measuring capacity, the existence of a hybrid can be determined. Another electrochemical detector measures faradaic current through DNA. DNA is comprised of organic and inorganic molecules that can inhibit current flow, and it is known that duplex DNA is a poorer insulator than single-stranded DNA. By introducing a redox couple and measuring the current at different electrodes with attached DNA, the existence of a duplex can be determined by noting an increase in current at a particular applied voltage.

Figure 9:
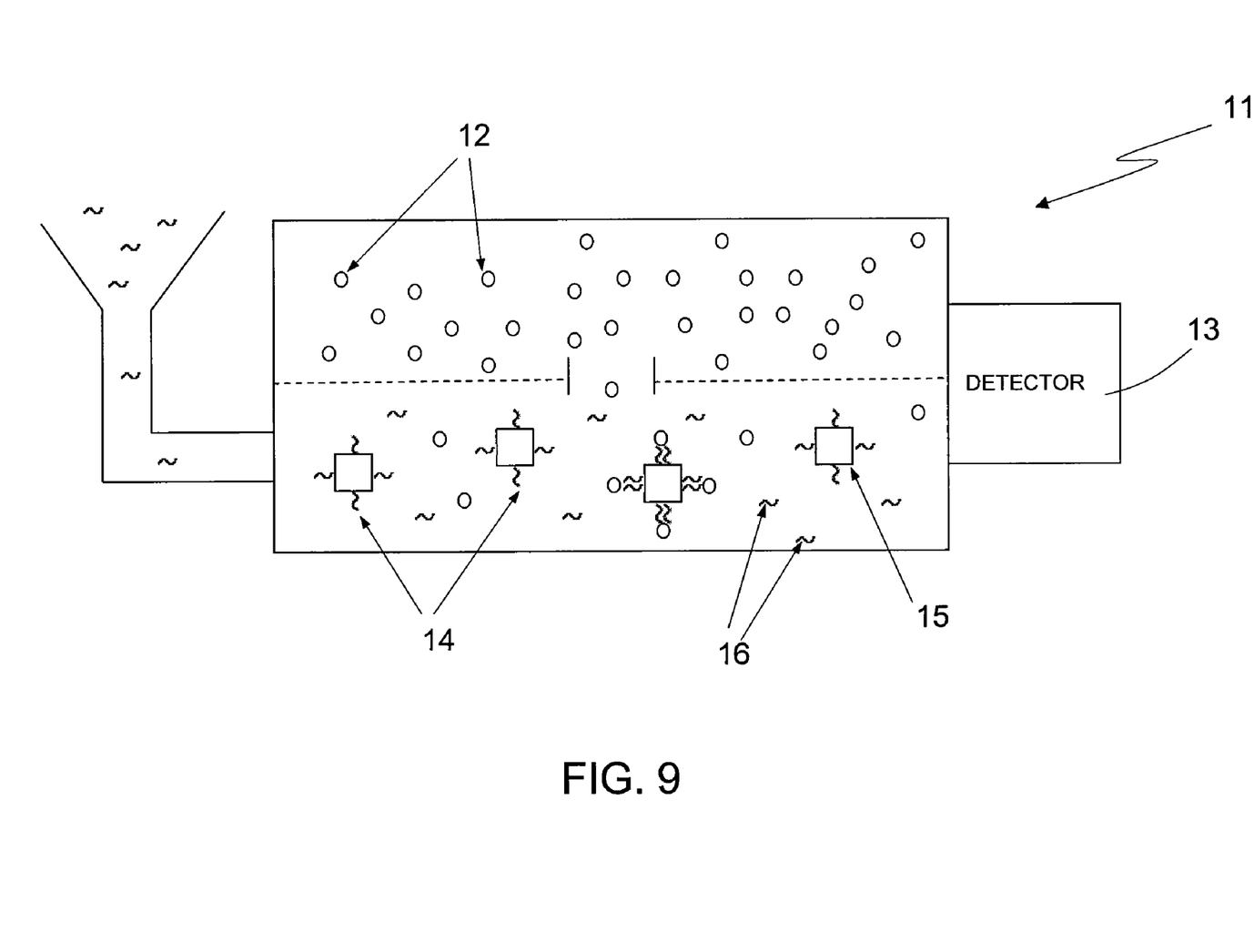
FIGS. 9 and 10 illustrate two embodiments of the system according to the present invention.

According to what is schematically illustrated in FIG. 9, the bifunctional compound 12 and the probes 14 are both contained in a common carrier means, for example a container, optionally divided into separate compartments that can be set in mutual communication, for example, at the moment of introduction of the sample nucleic acid 16, for instance using a separator diaphragm that can be severed (represented by the dashed line) on sample introduction.

Figure 10:
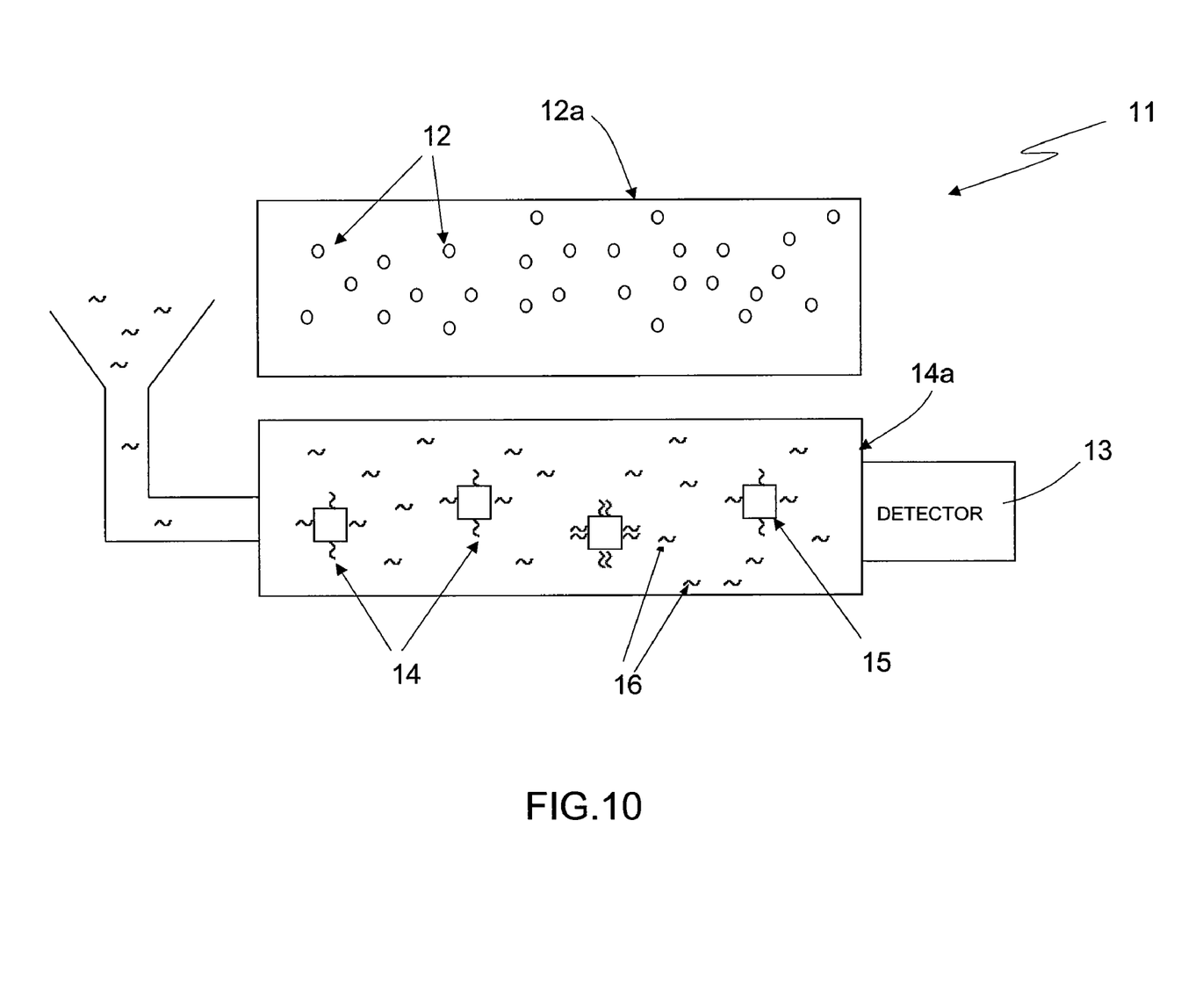

According to what is illustrated only schematically in FIG. 10, the bifunctional compound 12 and the probes 14 are each carried by respective carrier means, for example, defined by appropriate separate containers 12a, 14a forming part of a same kit, defining as a whole, together with the detector means 13, the system 11. At the moment of introduction of the sample nucleic acid 16, the bifunctional compound 12 is also introduced to the proximity of the probes 14 so as enable it to intercalate with the DNA during the hybridization step, for example by simply opening the corresponding container. In this embodiment, the containers are separated, but when needed, the content of container 12a is introduced into the container 14a in any obvious way.

In either case, the hybridization probes 14 can be immobilized on a support 15 for example defined by a solid surface forming part of the carrier means, e.g., of the container that contains also the bifunctional compound 12, or else they can be suspended in a solution, for example contained in the aforesaid container, either as such or else immobilized on a support 15 constituted, for example, by microspheres.

The invention is further described in the following examples with specific reference to the nature, structure, process of synthesis and functionality of the bifunctional compound 12, in an embodiment thereof constituted by the compound of Formula 1 as specified above.

EXAMPLE 1

Synthesis of Compound 1

The reaction of synthesis of the compound of Formula 1 is summarized in scheme 2.

500 mg of (anthracene-9-yl)methanol (M.W. 208.26 g/mol, 2.4 mmol) was solubilized in acetonitrile to obtain a yellow solution. The latter was heated under reflux (82° C.), and nitrogen was bubbled therein.

70 mg of sodium hydride (M.W. 24 g/mol, 2.9 mmol), previously washed with hexane and then suspended in acetonitrile, was added. After approximately 30 minutes, the mixture assumed a red coloring.

At this point, a solution prepared by solubilizing 1.3 g of α,α'-dibromium para-xylene (M.W. 263.97, 5 mmol) in acetonitrile was added. Reflux was maintained for 16 hours.

The reaction was followed via TLC (thin-layer chromatography) on silica using as eluent mixture cyclohexane/dichloromethane (1:2). Formation was thus noted of some by-products and of a very intense spot at Rf 0.77, as well as spots corresponding to the unreacted ingredients.

The spot at Rf 0.77 (compound A in scheme 2) was extracted with methanol, and the UV-VIS absorption spectrum determined. The spectrum showed the typical band for anthracene.

50 mg of 4,4'-bipyridyl (M.W. 156 g/mol, 0.32 mmol), solubilized in 20 ml of acetonitrile was prepared. This solution was heated under reflux, and small aliquots of a solution prepared by solubilizing 30 mg of the compound A in acetonitrile were added.

The reaction was again followed by silica TLC using a dichloromethane/methanol (1:1) eluant. After two hours the disappearance of the compound A (which was defective) was noted. The product (compound B, obtained according to the reaction illustrated in scheme 2) showed an Rf of 0.18.

Purification of compound B was carried out by anion exchange between Br- and PF6-; for this purpose, the reaction mixture was concentrated, and 3 ml of an NH4+PF6-saturated aqueous solution was added. Appearance of a pink precipitate was noted, and subsequently separated by filtration and washed with small portions of cold water.

Compound B (0.07 mmol) was then heat solubilized in chloroform/acetonitrile, and the temperature was kept at 40° C.

100 μl of methyl iodide was added and reacted with compound B at 40° C., and, additional aliquots of methyl iodide were added over the following 8 hours due to the volatility of the methyl iodide. After 24 h a silica TLC was carried out using dichloromethane/methanol (1:1) eluant, which highlighted an Rf=0 for compound 1.

EXAMPLE 2

Characterization of the Compound 1

The compound of Formula 1 was designed in such a way that the intercalating unit is photochemically inactive with regard to DNA, in order to prevent any damage thereto under conditions of ambient light.

Figure 2:
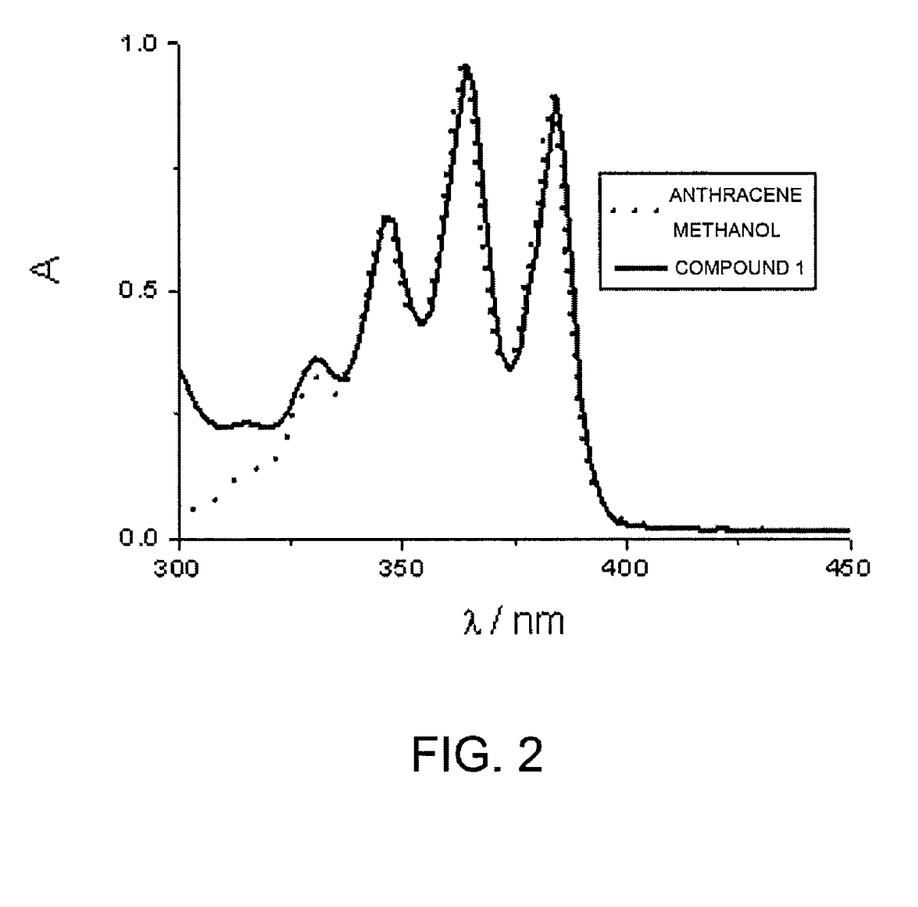
FIG. 2 illustrates the absorption spectra of the reference compound anthracene methanol and of the bifunctional compound of Formula 1, according to the invention.

FIG. 2 shows the absorption spectra of anthracene methanol, chosen as model reference compound, and of the bifunctional compound of Formula 1. The spectral similarity of the two traces clearly suggests the absence of interactions between the anthracene unit and viologen in the ground state.

Figure 3:
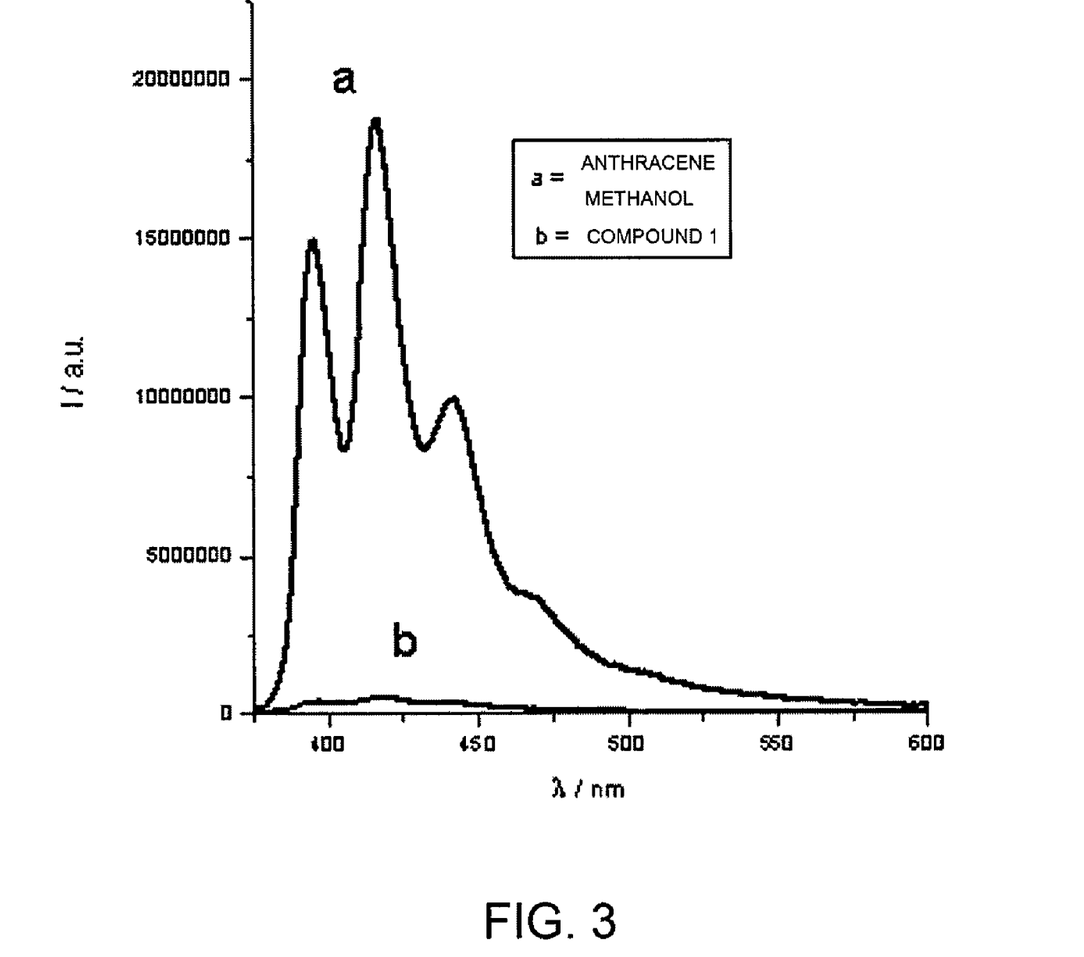
FIG. 3 illustrates the fluorescence spectra of reference compound anthracene methanol and of the compound of Formula 1.

Differences were instead encountered at the level of the excited states. FIG. 3 shows the fluorescence spectra of anthracene methanol and of the compound of Formula 1. As may be noted, the typical emission of the anthracene chromophore is totally deactivated in the compound of Formula 1 by the presence of the viologen group.

Figure 4:
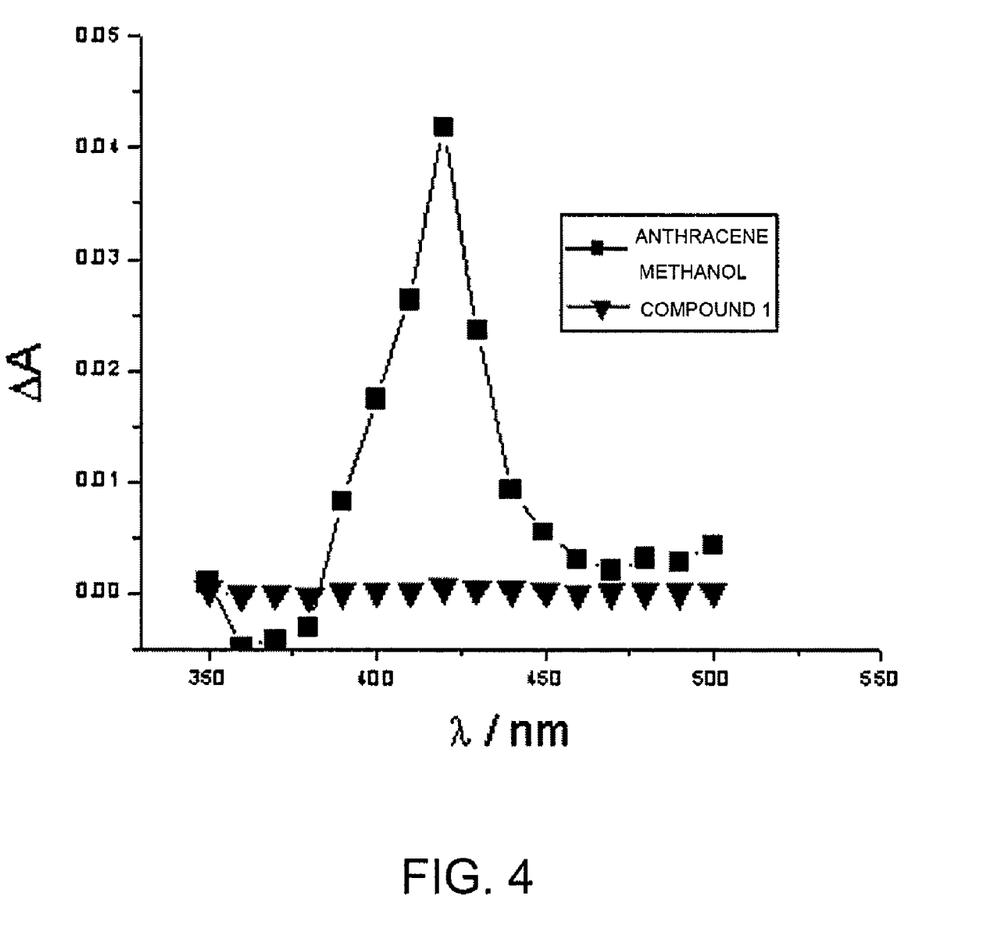
FIG. 4 illustrates the spectra of transient absorption recorded after the excitation-laser pulse of the reference compound anthracene methanol and of the compound of Formula 1.

Deactivation of the triplet state of the anthracene ring in the compound of Formula 1 was confirmed through flash laser photolysis experiments. FIG. 4 shows the spectra of transient absorption recorded 100 ns after the excitation-laser pulse in the case of anthracene methanol and the compound of Formula 1. In the first case the absorption observed is the typical signal of the lowest excited triplet state of anthracene. However, the triplet signal is altogether absent in the case of the compound of Formula 1, suggesting that the excited state is not populated. The quenching seen in the compound of Formula 1 can be ascribed to an effective process of thermodynamically favored photoinduced electron transfer between the excited anthracene and viologen.

EXAMPLE 3

Interaction Between Compound 1 and DSDNA

The high photostability of the compound of Formula 1 in the presence of DNA was demonstrated through flash laser photolysis experiments carried out at DNA concentrations that ensure 100% of binding of Formula 1 to DNA. The absence of a signal at 600 nm due to the reduced form of the viologen suggests that the return of the electrons from the viologen to the anthracene ring is the dominant process that regulates oxidation of the nucleobases from the oxidized form of anthracene.

The study of the interaction of the compound of Formula 1 with DNA is conducted by analysis of its absorption properties. In particular, the absorptions at the higher wavelengths enable observation of possible modifications following the addition of DNA without being affected by the absorption thereof, which terminates at approximately 300 nm.

Figure 5:
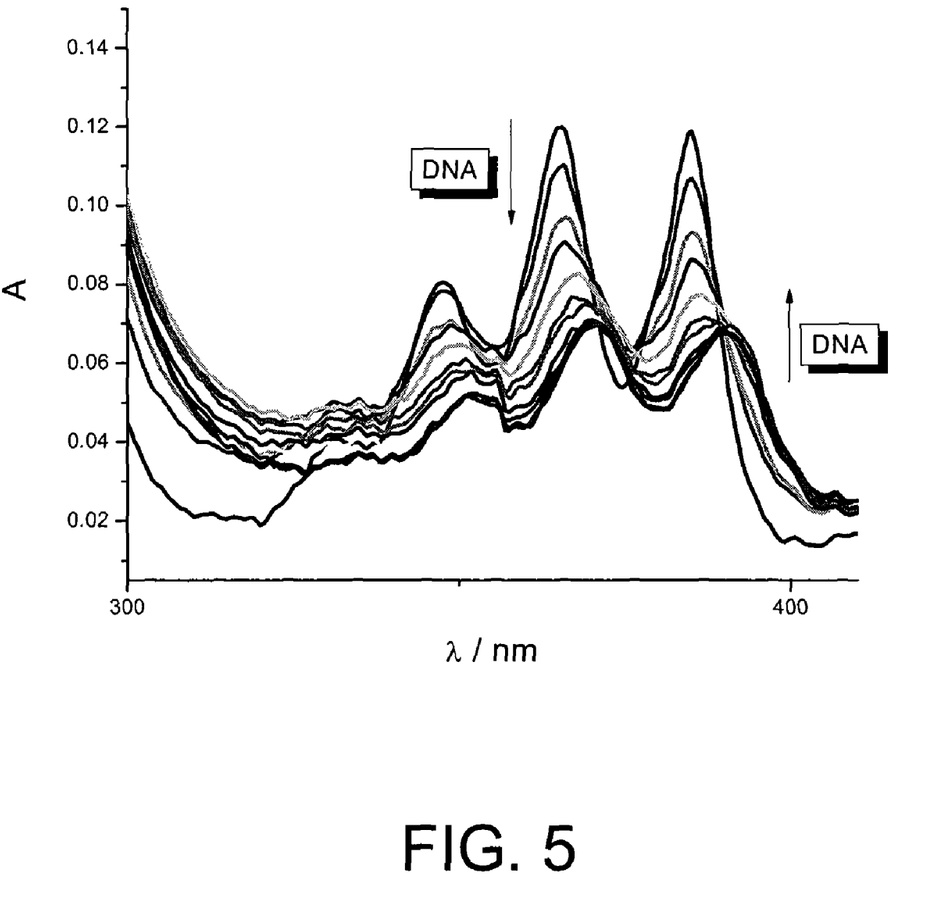
FIG. 5 illustrates the spectral variations observed in the absorption spectrum of the compound of Formula 1 following successive additions of calf thymus DNA.

FIG. 5 shows the spectral variation observed in the absorption spectrum of the compound of Formula 1 following successive additions of calf thymus DNA.

The results highlight how the presence of the DNA induces a considerable hypochromic and bathochromic effect on the spectrum. In particular, the three main bands at 347 nm, 365 nm and 384 nm decrease in intensity by more than 50% and at the same time shift towards the red. The considerable observed hypochromism is an index of a marked interaction between the electron states of the chromophore and those of the DNA nucleobases. Since the force of these interactions is expected to decrease with the cube of the distance of separation between the chromophore and the bases, the effect is an index of an intimate association between the anthracene chromophore and the DNA bases. The observed spectral variations are typical for intercalating polychromatic compounds and consequently suggest that the compound of Formula 1 is bound to the DNA principally through interactions of $\pi,\pi$ orbital overlapping.

The association constant, which has been calculated with the process studied by McGhee and Von Hippel (J. D. McGhee, P. H. von Hippel, J. Mol. Biol. (1974), vol. 86, pages 469-489), has a value of approximately $3.3 \times 10^5$. This value is one order of magnitude greater than the one reported in the literature both for anthracene (C. V. Kumar, E. H. Asuncion, Chem. Comm. (1992), page 470) and for viologen (D. W. Pang, H. D. Abruna, Anal. Chem. (2000), volume 72, pages 4700-4706) alone, indicating that the presence of viologen in the structure of the compound of Formula 1 not only modifies the intercalating properties of anthracene, but also significantly increases the effectiveness of the bond.

EXAMPLE 4

Interaction of Compound 1 with SSDNA and DSDNA

Figure 6:
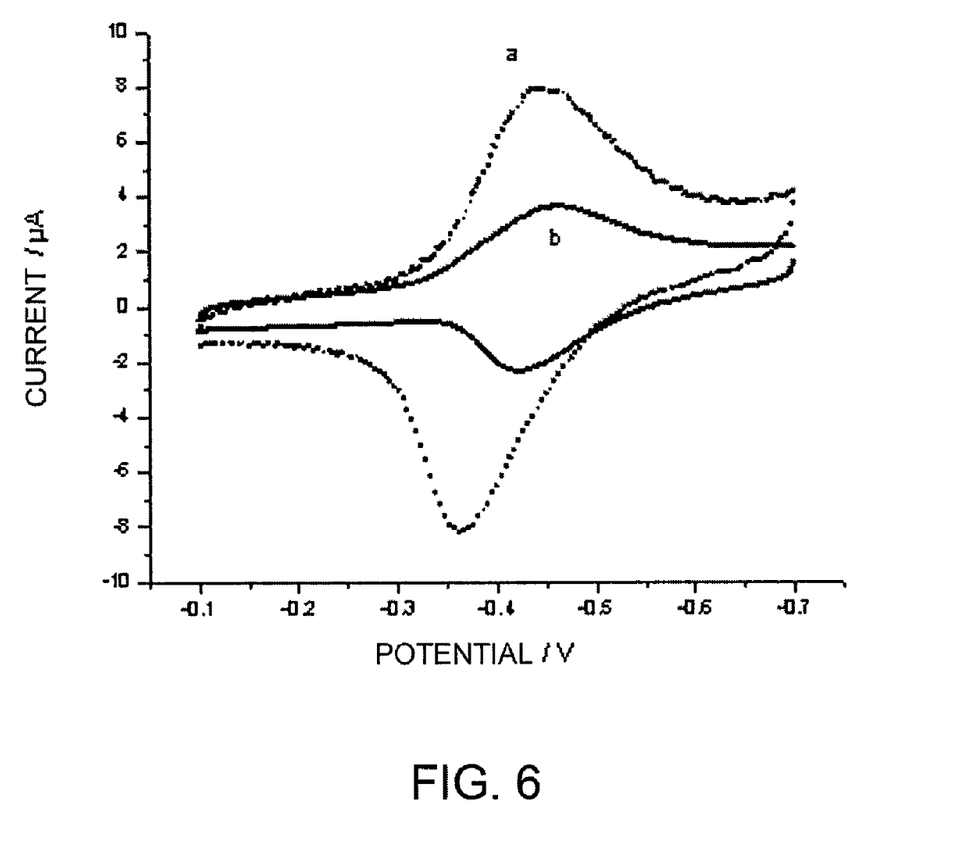
FIG. 6 illustrates the cyclic voltammogram of the compound of Formula 1 (40 µM) recorded on bare ITO electrodes (a) and of the compound of Formula 1 (2 µM) recorded on electrodes modified (b) with double-strand DNA.

FIG. 6 shows the voltammograms recorded in an aqueous solution of the compound of Formula 1 (40 μM) with bare ITO electrodes (a) and of the compound of Formula 1 (2 μM) on ITO electrodes modified (b) with double-strand DNA. The results clearly suggest that the reduction of the compound of Formula 1 in the case of modified electrodes is shifted towards negative values with respect to the ones observed in the case of bare electrodes. Consequently, it is believed that the interaction of the reduction-oxidation unit with the DNA is of an electrostatic type, as reported in the literature for viologen alone (D. W. Pang, H. D. Abruna, Anal. Chem., (2000), volume 72, pages 4700-4706.

Figure 7:
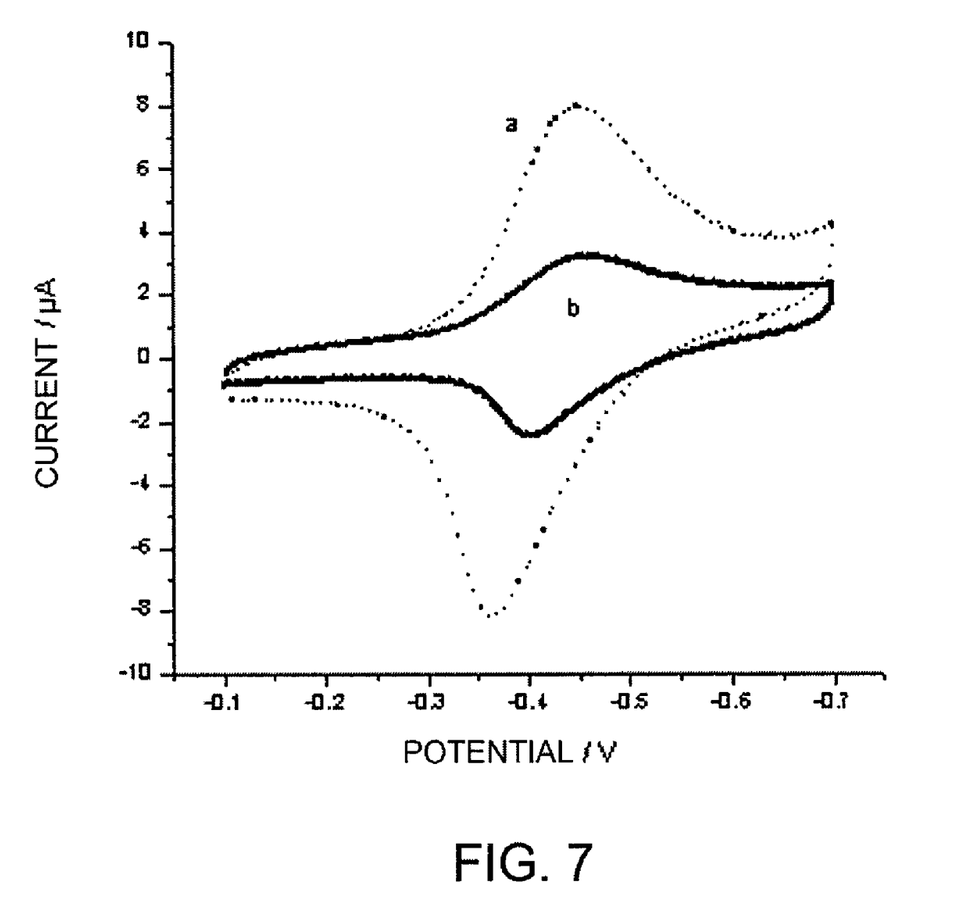
FIG. 7 illustrates the cyclic voltammogram of the compound of Formula 1 (40 µM) recorded on bare ITO electrodes (a) and of the compound of Formula 1 (2 µM) recorded on electrodes modified (b) with single-strand DNA.

FIG. 7 shows instead the cyclic voltammogram of the compound of Formula 1 (40 μM) recorded on bare ITO electrodes (a) and of the compound of Formula 1 (2 μM) recorded on electrodes modified (b) with single-strand DNA.

Also in this case, it clearly emerges that the reduction of the compound of Formula 1 in the case of modified electrodes is shifted towards negative values with respect to the ones observed in the case of non-modified electrodes. Consequently, this suggests that the interaction of the reduction-oxidation unit with the DNA is of an electrostatic type, as reported in the literature for viologen alone (D. W. Pang, H. D. Abruna, Anal. Chem., (2000), volume 72, pages 4700-4706).

However, from the shift, in either case it is demonstrated that the reduced and oxidized forms of the compound of Formula 1 exhibit a better affinity for DNA as compared to viologen alone.

Figure 8:
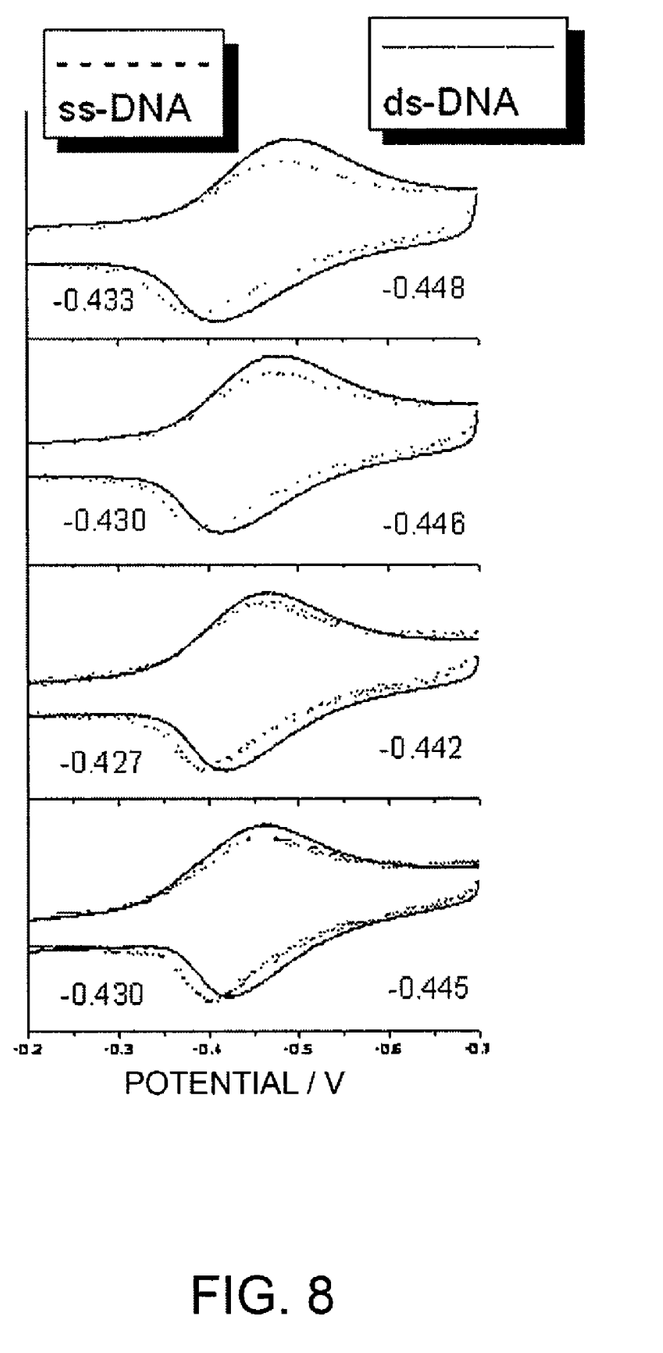
FIG. 8 illustrates the variations in the reduction potential of four different ITO electrodes modified with single-strand and double-strand DNA.

Finally, FIG. 8 shows the differences observed in the reduction potential of four different ITO electrodes modified with single-strand (dashed lines) and double-strand (solid lines) DNA. Even though the differences are small, they can be reproduced, thus indicating that the compound of Formula 1 is able to distinguish between the two different types of DNA structure.

What is claimed is:

1. A bifunctional compound, comprising a intercalating unit (I) that is capable of intercalating between nucleobases (B) of double strand nucleic acids and an active detection unit (AD) that is capable of emitting a detectable signal, characterized in that said active detection unit (AD) is selected from amongst chemical entities having a structure such as to interact electronically with said intercalating unit (I) in such a way that, during oxidation, the reduction-oxidation potential (EI+/I) of the semicouple I+/I defined by said intercalating unit (I) is lower than the reduction-oxidation potential (EB+/B) of the semicouple B+/B defined by said nucleobases (B), and in such a way that, during reduction, the reduction-oxidation potential (EI/I) of the semicouple I/I− defined by said intercalating unit (I) is higher than the reduction-oxidation potential (EB/B−) of the semicouple B/B− defined by said nucleobases (B), wherein the bifunctional compound comprises a spacer unit (S) set between said intercalating unit (I) and said active detection unit (AD) and said spacer unit (S) is an aliphatic chain substituted with derivatives of para-xylene.

2. The bifunctional compound according to claim 1, characterized in that said detectable signal is selected from the group consisting of a luminescent signal, a magnetic signal, an electrical signal, a thermal signal, an optical signal, an electronic signal, and an electrochemical signal.

3. The bifunctional compound of claim 1, characterized in that said intercalating unit (I) is selected from the group consisting of a naphthalene group, an anthracene group, a pyrene group, and a phenanthrene group.

4. The bifunctional compound according to claim 1, characterized in that said active detection unit (AD) is a viologen group.

5. The bifunctional compound of claim 1, having Formula 1:

(1)

6. A method for the detection of nucleic acids, the method comprising contacting the nucleic acid with the compound according to claim 1, and detecting a signal provided by the compound.

7. A method for the detection of nucleic acids, the method comprising contacting the nucleic acid with the compound according to claim 5, and detecting a signal provided by the compound.

8. The method according to claim 7, characterized in that said detecting is of an electrochemical type.

9. The method according to claim 8, characterized in that said nucleic acids are selected from the group consisting of single-strand DNA, double-strand DNA, or RNA.

10. The method according to claim 6, characterized in that it is performed in conjunction with that of hybridization probes immobilized on a solid surface.

11. The method according to claim 6, characterized in that it is performed in conjunction with that of hybridization probes suspended in a solution.

12. A process for the preparation of a bifunctional compound, comprising the steps of:

a) reacting a compound of Formula 2:

(2)

where n is 0-10 with a para-xylene substituted in the positions α,α' with a halogen in the presence of sodium hydride to obtain a compound of Formula 3:

(3)

where X is a halogen;
reacting said compound of Formula 3 with a 4,4'-bipyridyl to obtain a compound of Formula 5:

and reacting said compound of Formula 5 with a halogenated derivative of methane to obtain said compound of Formula 1:

13. A system for detection of nucleic acids comprising a bifunctional compound according to claim 5, the system comprising electrochemical means for detecting a signal emitted by said compound.

14. The system according to claim 13, characterized in that the system further comprises nucleic acid probes immobilized on a support.

15. The system according to claim 14, characterized in that the system further comprises physical carrier means for said bifunctional compound and for said nucleic acid probes.

16. A compound having Formula 1:

* * * * *